(12) United States Patent
Fobare et al.

(10) Patent No.: US 7,459,567 B2
(45) Date of Patent: Dec. 2, 2008

(54) SUBSTITUTED THIENYL AND FURYL ACYLGUANIDINES AND METHODS OF THEIR USE AS BETA-SECRETASE MODULATORS

(75) Inventors: William Floyd Fobare, Lawrenceville, NJ (US); William Ronald Solvibile, Jr., East Windsor, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/352,646

(22) Filed: Feb. 13, 2006

(65) Prior Publication Data

US 2006/0183792 A1    Aug. 17, 2006

Related U.S. Application Data

(60) Provisional application No. 60/652,669, filed on Feb. 14, 2005.

(51) Int. Cl.
*C07D 333/02*    (2006.01)
*A01N 43/02*    (2006.01)

(52) U.S. Cl. ................................ 549/29; 514/430

(58) Field of Classification Search ............ 549/29; 514/430

See application file for complete search history.

(56) References Cited

FOREIGN PATENT DOCUMENTS

| | | | |
|---|---|---|---|
| EP | 0 861 831 A1 | 9/1998 | |
| GB | 2 013 192 A | 8/1979 | |

OTHER PUBLICATIONS

MayoClinic.com, Alzheimer's disease: Cause (1 page).*
Vandana et al., Journal of drug targeting (2005), vol. 13, abstract.*
Su et al.; Expert opinion on drug delivery (May 2006) vol. 3, abstract.*
Lefrance-Jullien et al., British Journal of Pharmacology (2005), 145, 228-235.*
Fact Sheet, Alzheimer's Association, 2006.*
Abbott et al., Molecular Medicine Today (1996), vol. 2, p. 106-113.*

* cited by examiner

*Primary Examiner*—Kamal Saeed
*Assistant Examiner*—Sun Yae Y Loewe
(74) *Attorney, Agent, or Firm*—Ram W. Sabnis; Scott K. Larsen

(57) ABSTRACT

The present invention provides a substituted thienyl or furyl acylguanidine compound of formula I

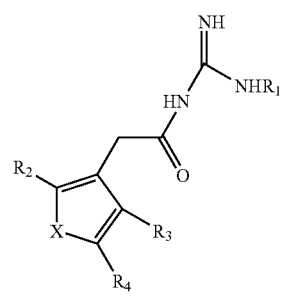

The present invention also provides methods for the inhibition of β-secretase (BACE) and for the treatment of β-amyloid deposits and neurofibrillary tangles.

12 Claims, No Drawings

SUBSTITUTED THIENYL AND FURYL ACYLGUANIDINES AND METHODS OF THEIR USE AS BETA-SECRETASE MODULATORS

BACKGROUND

This application claims the benefit under 35 U.S.C. §119(e) to co-pending U.S. Provisional Application No. 60/652,669, filed Feb. 14, 2005, which is hereby incorporated by reference in its entirety.

β-Amyloid deposits and neurofibrillary tangles are two major pathologic characterizations associated with Alzheimer's disease (AD). Clinically, AD is characterized by the of loss of memory, cognition, reasoning, judgment, and orientation. Also affected, as the disease progresses, are motor, sensory, and linguistic abilities until global impairment of multiple cognitive functions occurs. These cognitive losses take place gradually, but typically lead to severe impairment and eventual death in 4-12 years.

Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders. (Varghese, J., et al, Journal of Medicinal Chemistry, 2003, 46, 4625-4630).

β-Amyloid deposits are predominately an aggregate of Aβ peptide, which in turn is a product of the proteolysis of amyloid precursor protein (APP). More specifically, Aβ peptide results from the cleavage of APP at the C-terminus by one or more γ-secretases, and at the N-terminus by β-secretase enzyme (BACE), also known as aspartyl protease, as part of the β-amyloidogenic pathway.

BACE activity is correlated directly to the generation of Aβ peptide from APP (Sinha, et al, Nature, 1999, 402, 537-540), and studies increasingly indicate that the inhibition of BACE inhibits the production of Aβ peptide. (Roberds, S. L., et al, Human Molecular Genetics, 2001, 10, 1317-1324).

Therefore, it is an object of this invention to provide compounds which are inhibitors of β-secretase and are useful as therapeutic agents in the treatment, prevention or amelioration of a disease or disorder characterized by elevated β-amyloid deposits or β-amyloid levels in a patient.

It is another object of this invention to provide therapeutic methods and pharmaceutical compositions useful for the treatment, prevention or amelioration of a disease or disorder characterized by elevated β-amyloid deposits or β-amyloid levels in a patient.

It is a feature of this invention that the compounds provided may also be useful to further study and elucidate the β-secretase enzyme.

These and other objects and features of the invention will become more apparent by the detailed description set forth hereinbelow.

SUMMARY

The present invention provides a compound of formula I

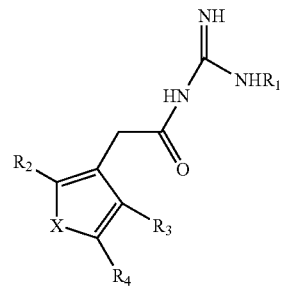

wherein
X is O or S;
$R_1$ is hydrogen or an alkyl, alkenyl, alkoxy, cycloalkyl, cycloalkenyl, cycloheteroalkyl, alkyl ester, aryl, or heteroaryl group each optionally substituted;
$R_2$ and $R_3$ are each independently an aryl, heteroaryl, cycloheteroalkyl, cycloalkyl, or cycloalkenyl group each group optionally substituted;
$R_4$ is hydrogen, halogen, CHO, CN, $COOR_5$, $CONR_6R_7$, $NO_2$, $SO_nR_5$, OH, $NR_6R_7$ or an alkyl or cycloalkyl group each group optionally substituted;
n is 0, 1 or 2;
$R_5$ is hydrogen or an alkyl, alkoxy, cycloalkyl, cycloalkenyl, cycloheteroalkyl, aryl, alkyl ester, or heteroaryl group each optinally substituted; and
$R_6$ and $R_7$ are each independently hydrogen or an alkyl, alkoxy, cycloalkyl, cycloalkenyl, cycloheteroalkyl, aryl, alkyl ester or heteroaryl group each group optionally substituted or $R_6$ and $R_7$ may be taken together with the atom to which they are attached to form an optionally substituted 5- to 7-membered ring optionally containing an additional heteroatom selected from N, O or S; or a tautomer thereof, a stereoisomer thereof or a pharmaceutically-acceptable salt thereof.

The present invention also relates to the use of substituted thienyl and furyl acylguanidine compounds for the treatment of β-amyloid deposits and neurofibrillary tangles. These compounds are particularly useful in treating Alzheimer's disease, cognitive impairment, Down's Syndrome, HCHWA-D, cognitive decline, senile dementia, cerebral amyloid angiopathy, degenerative dementia, or other neurodegenerative disorders.

DETAILED DESCRIPTION

Alzheimer's disease (AD) is a major degenerative disease of the brain which presents clinically by progressive loss of memory, cognition, reasoning, judgement and emotional stability and gradually leads to profound mental deteoriation and death. The exact cause of AD is unknown, but increasing evidence indicates that amyloid beta peptide (A-beta) plays a central role in the pathogenesis of the disease. (D. B. Schenk; R. E. Rydel et al, Journal of Medicinal Chemistry, 1995, 21,4141 and D. J. Selkoe, Physiology Review, 2001, 81, 741). Patients with AD exhibit characteristic neuropathological markers such as neuritic plaques (and in β-amyloid angiopathy, deposits in cerebral blood vessels) as well as neurofibrillary tangles detected in the brain at autopsy. A-beta is a major component of neuritic plaques in AD brains. In addition, β-amyloid deposits and vascular β-amyloid angiopathy also characterize individuals with Downs Syndrome, Hereditary Cerebral Hemmorhage with Amyloidosis of the Dutch type and other neurodegenreative and dementia-inducing disorders. Over expression of the amyloid precursor protein (APP), altered cleavage of APP to A-beta or a decrease in the clearance of A-beta from a patient's brain may increase the levels of soluble or fibrullar forms of A-beta in the brain. The β-site APP cleaving enzyme, BACE1, also called memapsin-2 or Asp-2, was identified in 1999 (R. Vassar, B. D. Bennett, et al, Nature, 1999, 402, 537). BACE1 is a membrane-bound aspartic protease with all the known functional properties and characteristics of β-secretase. Low molecular weight, non-peptide, non-substrate-related inhibitors of BACE1 or β-secretase are earnestly sought both as an aid in the study of the β-secretase enzyme and as potential therapeutic agents.

Surprisingly, it has now been found that a thienyl or furyl acylguanidine of formula I demonstrates inhibition of β-secretase and the selective inhibition of BACE1. Advantageously, said acylguanidine compounds may be used as effective therapeutic agents for the treatment, prevention or amelioration of a disease or disorder characterized by elevated β-amyloid deposits or β-amyloid levels in a patient. Accordingly, the present invention provides a thienyl or furyl acyguanidine compound of formula I

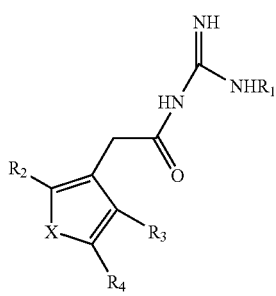

wherein

X is O or S;

$R_1$ is hydrogen or an alkyl, alkenyl, alkoxy, cycloalkyl, cycloalkenyl, cycloheteroalkyl, alkyl ester, aryl, or heteroaryl group each optionally substituted;

$R_2$ and $R_3$ are each independently an aryl, heteroaryl, cycloheteroalkyl, cycloalkyl, or cycloalkenyl group each group optionally substituted;

$R_4$ is hydrogen, halogen, CHO, CN, $COOR_5$, $CONR_6R_7$, $NO_2$, $SO_nR_5$, OH, $NR_6R_7$ or an alkyl or cycloalkyl group each group optionally substituted;

n is 0, 1 or 2;

$R_5$ is hydrogen or an alkyl, alkoxy, cycloalkyl, cycloalkenyl, cycloheteroalkyl, aryl, alkyl ester, or heteroaryl group each optinally substituted; and $R_6$ and $R_7$ are each independently hydrogen or an alkyl, alkoxy, cycloalkyl, cycloalkenyl, cycloheteroalkyl, aryl, alkyl ester or heteroaryl group each group optionally substituted or $R_6$ and $R_7$ may be taken together with the atom to which they are attached to form an optionally substituted 5- to 7-membered ring optionally containing an additional heteroatom selected from N, O or S; or a tautomer thereof, a stereoisomer thereof or a pharmaceutically-acceptable salt thereof.

Unless stated otherwise, each alkyl, alkoxy, alkenyl, alkynyl, cycloalkyl, cycloalkenyl, cycloheteroalkyl, aryl, alkyl ester or heteroaryl group is contemplated as being optionally substituted.

An optionally substituted moiety may be substituted with one or more substituents. The substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Unless otherwise specified, typically, 0-4 substituents may be present. When any of the foregoing substituents represents or contains an alkyl substituent group, this may be linear or branched and may contain up to 12 carbon atoms, preferably up to 6 carbon atoms, more preferably up to 4 carbon atoms.

As used herein, the term "alkyl" includes both ($C_1$-$C_{12}$) straight chain and ($C_3$-$C_{12}$) branched-chain monovalent saturated hydrocarbon moiety. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, and the like.

The term "alkenyl", as used herein, means either a ($C_2$-$C_{10}$) straight chain or ($C_3$-$C_{10}$) branched-chain monovalent hydrocarbon moiety containing at least one double bond. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), and higher homologs, isomers, and the like.

The term "cycloalkyl" as used herein means a monocyclic, bicyclic, tricyclic, fused, bridged, or spiro monovalent saturated hydrocarbon moiety of 3-10 carbon atoms, wherein the carbon atoms are located inside or outside of the ring system. Any suitable ring position of the cycloalkyl moiety may be covalently linked to the defined chemical structure. Examples of cycloalkyl moieties include, but are not limited to, chemical groups such as cyclopropyl, cyclopropylmethyl, cyclobutyl, cyclopentyl, cyclohexyl, cyclohexylmethyl, cyclohexylethyl, cycloheptyl, norbornyl, adamantyl, spiro[4.5]decanyl, and homologs, isomers, and the like.

The term "cycloalkenyl" includes cyclized alkyl chains containing an alkenyl group having the specified number of carbon atoms, e.g., cyclopentenyl, cyclohexenyl, etc. The term "cycloalkenyl" further includes both unsubstituted and mono-, di- or tri-substituted hydrocarbon groups.

The term "alkoxy", as used herein, means either a ($C_1$-$C_{10}$) straight chain or ($C_3$-$C_{10}$) branched-chain hydrocarbon covalently bonded to an oxygen atom. Examples of alkoxys include, but are not limited to, chemical groups such as methoxy, ethoxy, isopropoxy, sec-butoxy, tert-butoxy, decanoxy, and homologs, isomers, and the like.

The term "halogen" includes fluorine, chlorine, iodine, and bromine.

The term "haloalkyl" as used herein designates a $C_nH_{2n+1}$ group having from one to 2n+1 halogen atoms which may be the same or different and the term "haloalkoxy" as used herein designates an $OC_nH_{2n+1}$ group having from one to 2n+1 halogen atoms which may be the same or different.

The term "aryl" means an aromatic carbocyclic moiety of up to 20 carbon atoms, which may be a single ring (monocyclic) or multiple rings (bicyclic, up to three rings) fused together or linked covalently. Examples of aryl moieties include, but are not limited to, chemical groups such as phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like. The term "aryl" further includes both unsubstituted carbocylic groups and carbocyclic groups containing 1-5-substitutions.

The term "heteroaryl" as used herein means an aromatic heterocyclic ring system, which may be a single ring (monocyclic) or multiple rings (bicyclic, up to three rings) fused together or linked covalently. The rings may contain from one to four hetero atoms selected from nitrogen, oxygen, or sulfur, wherein the nitrogen or sulfur atom(s) are optionally oxidized, or the nitrogen atom(s) are optionally quarternized. Examples of heteroaryl moieties include, but are not limited to, heterocycles such as furan, thiophene, pyrrole, pyrazole, imidazole, oxazole, isoxazole, thiazole, isothiazole, 1H-tetrazole, 1,3,4-oxadiazole, 1H-1,2,4-triazole, 1,3,4-triazole, pyridine, pyrimidine, pyrazine, pyridazine, benzoxazole, benzisoxazole, benzothiazole, benzofuran, benzothiophene, thianthrene, dibenzo[b,d]furan, dibenzo[b,d]thiophene, benzimidazole, indole, indazole, quinoline, isoquinoline, quinazoline, quinoxaline, purine, pteridine, 9H-carbazole, β-carboline, or the like.

The term "cycloheteroalkyl" as used herein designates a 5-7 membered ring system containing 1 or 2 heteroatoms, which may be the same or different, selected from nitrogen, oxygen and sulfur and optionally containing one double bond. Exemplary of the cycloheteroalkyl ring systems included in the term as designated herein are the following rings wherein $X_1$ is NR, O or S; and R is H or an optional substituent as described hereinbelow:

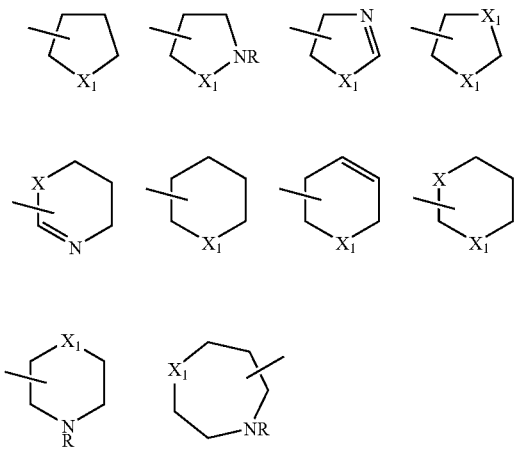

The term "alkyl ester", as used herein, means either a $(C_1-C_{10})$ straight chain or $(C_3-C_{10})$ branched-chain hydrocarbon covalently bonded to a carboxylic acid. Examples of alkyl esters include, but are not limited to, chemical groups such as methyl formate, methyl acetate, ethyl propanoate, ethyl butanoate, and the like.

The compounds of the present invention can be converted to salts; in particular pharmaceutically acceptable salts using art recognized procedures. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethyl-propylamine, or a mono-, di-, or trihydroxy lower alkylamine, for example mono-, di- or triethanolamine. Internal salts may furthermore be formed. Salts which are unsuitable for pharmaceutical uses but which can be employed, for example, for the isolation or purification of free compounds or their pharmaceutically acceptable salts, are also included. The term "pharmaceutically acceptable salt", as used herein, refers to salts derived form organic and inorganic acids such as, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

The carbon number as used in the definitions herein refers to carbon backbone and carbon branching, but does not include carbon atoms of the substituents, such as alkoxy substitutions and the like.

Tautomers often exist in equilibrium with each other. As these tautomers interconvert under environmental and physiological conditions, they provide the same useful biological effects. The present invention encompasses mixtures of such tautomers.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof. Where a stereoisomer is preferred, it may in some embodiments be provided substantially free of the corresponding enantiomer. Thus, an enantiomer substantially free of the corresponding enantiomer refers to a compound that is isolated or separated via separation techniques or prepared free of the corresponding enantiomer. "Substantially free", as used herein, means that the compound is made up of a significantly greater proportion of one stereoisomer, preferably less than about 50%, more preferably less than about 75%, and even more preferably less than about 90%.

Preferred compounds of the invention are those compounds of formula I wherein X is S. Also preferred are those compounds of formula I wherein $R_1$ is hydrogen or an optionally substituted alkyl group. Another group of preferred compounds of the invention are those compounds of formula I wherein $R_2$ and $R_3$ are each independently an optionally substituted aryl group.

More preferred compounds of the invention are those compounds of formula I wherein X is S and $R_1$ is hydrogen or an alkyl group optionally substituted with hydroxy. Another group of more preferred compounds are those compounds of formula I wherein X is S and $R_2$ and $R_3$ are each independently an optionally substituted aryl group. A further group of more preferred compounds are those compounds of formula I wherein X is S; $R_1$ is hydrogen or an alkyl group optionally substituted with hydroxy; $R_2$ and $R_3$ are each independently a phenyl group optionally substituted with one halogen, alkoxy, haloalkoxy, aryloxy or $CONHR_7$; and $R_4$ is hydrogen.

Preferred compounds of the invention include:
N"-{[4-(2-chlorophenyl)-2-(4-propoxyphenyl)thien-3-yl]acetyl}guanidine;
N"-[(2,4-diphenylthien-3-yl)acetyl]guanidine;
N"-{[2-(4-phenoxyphenyl)-4-phenylthien-3-yl]acetyl}guanidine;
N"-{[4-(2-chlorophenyl)-2-(4-phenoxyphenyl)thien-3-yl]acetyl}guanidine;
N"-{[2-(2-chlorophenyl)-4-(4-propoxyphenyl)thien-3-yl]acetyl}guanidine;
N"-({2-(4-propoxyphenyl)-4-[2-(trifluoromethoxy)phenyl]thien-3-yl}acetyl)guanidine;
N-{[4-phenyl-2-(4-propoxyphenyl)thien-3-yl]acetyl}guanidine;
N"-{[2-phenyl-4-(4-propoxyphenyl)thien-3-yl]acetyl}guanidine;
N"-{[2-[4-(4-acetylphenoxy)phenyl]-4-(2-chlorophenyl)thien-3-yl]acetyl}guanidine;
N"-({4-(2-chlorophenyl)-2-[4-(4-propionylphenoxy)phenyl]thien-3-yl}acetyl)guanidine;
2-(4-(2-chlorophenyl)-2-{4-[2-(1H-pyrazol-4-yl)ethoxy]phenyl}thien-3-yl)-N-(diaminomethylene)acetamide;
2-[4-(2-chlorophenyl)-2-(4-propoxyphenyl)thien-3-yl]-N-[[(3-hydroxypropyl)amino](imino)methyl]acetamide;
4-[4-(2-chlorophenyl)-3-(2-{[[(3-hydroxypropyl)amino](imino)methyl]amino}-2-oxoethyl)thien-2-yl]-N-(1-ethylpropyl)benzamide;
4-[4-(2-chlorophenyl)-3-(2-{[[(3-hydroxypropyl)amino](imino)methyl]amino}-2-oxoethyl)thien-2-yl]-N-(2,2,2-trifluoroethyl)benzamide;
4-[4-(2-chlorophenyl)-3-(2-{[[(3-hydroxypropyl)amino](imino)methyl]amino}-2-oxoethyl)thien-2-yl]-N-propylbenzamide;
4-[4-(2-chlorophenyl)-3-(2-{[[(3-hydroxypropyl)amino](imino)methyl]amino}-2-oxoethyl)thien-2-yl]-N-(cyclopropylmethyl)benzamide;
N-butyl-4-[4-(2-chlorophenyl)-3-(2-{[[(3-hydroxypropyl)amino](imino)methyl]amino}-2-oxoethyl)thien-2-yl]benzamide;
2-[4-(2-chlorophenyl)-2-(3-methyl-4-propoxyphenyl)thien-3-yl]-N-[[(3-hydroxypropyl)amino](imino)methyl]acetamide;
2-[4-(2-chlorophenyl)-2-(2-methyl-4-propoxyphenyl)thien-3-yl]-N-[[(3-hydroxypropyl)amino](imino)methyl]acetamide;

a tautomer thereof, a stereoisomer thereof or a pharmaceutically acceptable salt thereof.

The compounds of the invention may be prepared according to the following reaction schemes or modifications thereof using readily available starting materials, reagents and conventional synthetic procedures. It is also possible to make use of variants of these process Steps, which in themselves are known to and well within the preparatory skill of the medicinal chemist. The reagents used in the preparation of the compounds of this invention can be either commercially obtained or can be prepared by standard procedures described in the literature.

Starting with the commercially available 3-methyl-2,4,5-tribromothiophene (Scheme 1) in tetrahydrofuran (THF) at −78° C. and reacting with 1.05 equivalents of n-butyllithium for 15 minutes and quenching with water yields the 2,4-dibromo-3-methylthiophene 1. Radical bromination of the methyl group of 1 with 1.1 equivalents of n-bromosuccinimide in carbon tetrachloride and a catalytic amount of azo-bis-isobutyronitrile (AIBN) under reflux with a 500 W sunlamp gives the 2,4-dibromo-3-(bromomethyl)thiophene 2. Cyanide displacement of the alkyl bromide with potassium cyanide in ethanol/water yielded the corresponding nitrile 3. Hydrolysis of the nitrile with catalytic sulfuric acid in alcohol, such as methanol or ethanol, yielded the corresponding ester 4.

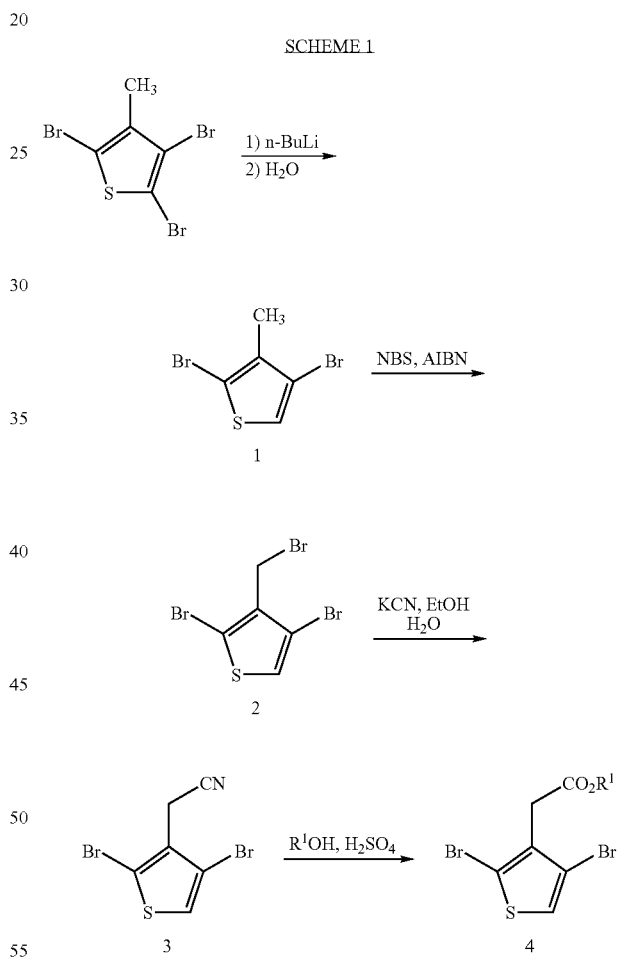

SCHEME 1

Differential Suzuki couplings on the dibomo-substituted thiophene 4 occurs with reaction of 1.05 equivalents of an aryl-boronic acid or arylboronate ester with a base and a palladium catalyst at position 2 of the thiophene (Scheme 2) to give the corresponding 2-arylsubstituted thiophene 5 (Scheme 2). A second Suzuki coupling occurs when 1.5 equivalents of an aryl-boronic acid or arylboronate with a palladium catalyst and a base react with the 4-bromothiophene compound 5. Saponification of the ester yields the acid 7. Activation of the acid with cabonyl diimidazole (CDI) and reaction with guanidine hydrochloride and base yields the requisite 2,3,4-trisubstitutedthienylacyl guanidine.

SCHEME 2

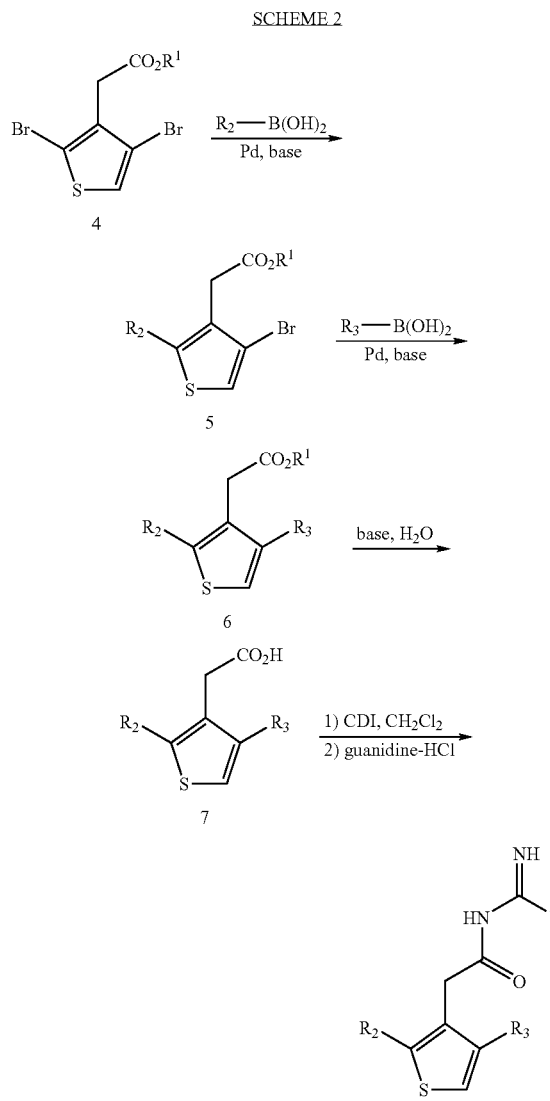

An alternative synthesis of $R_1$-substituted analogs is outlined in Scheme 3. Reaction of the acid 7 with CDI and base followed by 1-H-pyrazole-1-carboxamidine hydrochloride yields the substituted thiophene 8. The pyrazole activated acyl-amidine reacts with a substituted amine to give the requisite product.

SCHEME 3

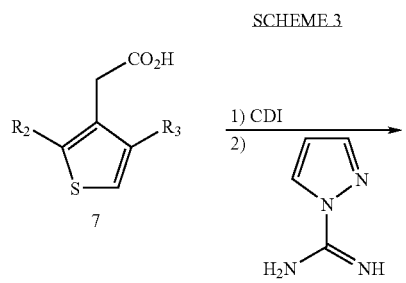

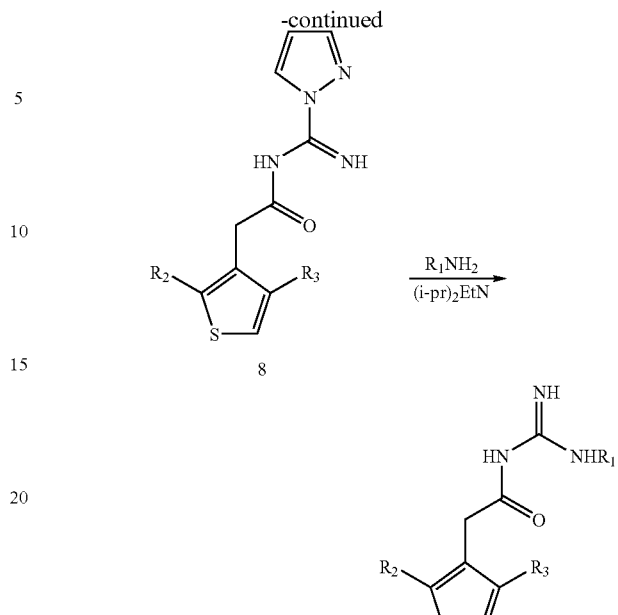

Advantageously, the formula I compounds of the invention act as BACE inhibitors for the treatment of β-amyloid deposits and neurofibrillary tangles associated with such diseases as Alzheimer's disease, Trisomy 21 (Down's Syndrome), Hereditary Cerebral Hemorrhage with Amyloidosis of the Dutch-type (HCHWA-D), and other neurodegenerative disorders. Accordingly this invention provides methods for modulating BACE and treating, preventing, or ameliorating β-amyloid deposits and neurofibrillary tangles associated with diseases and disorders such as Alzheimer's disease, Trisomy 21 (Down's Syndrome), Hereditary Cerebral Hemorrhage with Amyloidosis of the Dutch-type (HCHWA-D), and other neurodegenerative disorders. Such methods generally involve providing to a patient suspected of suffering from, or being susceptible to, the disease or injury an effective amount of a compound of formula I. Also according to the present invention there is provided a method of treating Alzheimer's disease and related senile dementia's in humans or other mammals which comprises providing to a human or other mammal an effective amount of a compound of the present invention.

The present invention also provides methods for treating a patient suspected of suffering from a disease associated with excessive BACE activity, comprising the Step of providing to the patient an effective amount of at least one compound of Formula I. Representative diseases include Alzheimer's disease, cognitive impairment, Down's Syndrome, HCHWA-D, cognitive decline, senile dementia, cerebral amyloid angiopathy, degenerative dementia, or other neurodegenerative disorders. Certain of these diseases are characterized by production of β-amyloid deposits or neurofibrillary tangles.

The present invention also provides methods for modulating (and, preferably, inhibiting) the activity of BACE, comprising providing to a patient and/or contacting a receptor thereof with an effective amount of at least one compound of Formula I.

As used in accordance with this invention, the term "providing," with respect to providing a compound or substance covered by this invention, means either directly administering such a compound or substance, or administering a prodrug, derivative, or analog which will form the effective amount of the compound or substance within the body. This invention also covers providing the compounds of this invention to treat the disease states disclosed herein that the compounds are useful for treating.

The term "patient", as used herein, refers to a mammal, preferably a human.

The terms "effective amount", "therapeutically effective amount" and "effective dosage" as used herein, refer to the amount of a compound that, when administered to a patient, is effective to at least partially ameliorate (and, in preferred embodiments, cure) a condition form which the patient is suspected to suffer.

In one aspect, the present invention is directed to compositions comprising one or more compounds of formula I and one or more pharmaceutically acceptable carriers.

Accordingly the present invention provides a pharmaceutical composition comprising an effective amount of a compound of formula I and a pharmaceutically acceptable carrier.

The term "carrier", as used herein, shall encompass carriers, excipients, and diluents. Examples of carriers are well known to those skilled in the art and are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

Applicable solid carriers can include one or more substances which may also act as flavoring agents, lubricants, solubilizers, suspending agents, fillers, glidants, compression aids, binders or tablet-disintegrating agents or encapsulating materials. They are formulated in conventional manner, for example, in a manner similar to that used for known antihypertensive agents, diuretics and β-blocking agents. Oral formulations containing the active compounds of this invention may comprise any conventionally used oral forms, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. The powders and tablets preferably contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colliodol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or fruit juice, containing appropriate solubilizers or emulisifiers as needed.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration may be in either liquid or solid form.

Preferably the pharmaceutical composition is in unit dosage form, e.g., as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. Such administrations may be carried out using the present compounds, or pharmaceutically acceptable salts thereof, in lotions, creams, foams, patches, suspensions, solutions, and suppositories (rectal and vaginal).

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic application, compounds of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

The terms "administer", "administering", or "administration", as used herein, refer to either directly administering a compound or composition to a patient, or administering a prodrug derivative or analog of the compound to the patient, which will form an equivalent amount of the active compound or substance within the patient's body.

It is understood that the effective dosage of the active compounds of this invention may vary depending upon the particular compound utilized, the mode of administration, the condition, and severity thereof, of the condition being treated, as well as the various physical factors related to the individual being treated. For treating Alzheimer's disease and other related senile dementia's, generally, satisfactory results may be obtained when the compounds of this invention are administered to the individual in need at a daily dosage of from about 0.1 mg to about 1 mg per kilogram of body weight, preferably administered in divided doses two to six times per day, or in a sustained release form. For most large mammals, the total daily dosage is from about 3.5 mg to about 140 mg preferably from about 3.5 to about 5 mg. In the case of a 70 kg human adult, the total daily dose will generally be from about 7 mg to about 70 mg and may be adjusted to provide the optimal therapeutic result. This regimen may be adjusted to provide the optimal therapeutic response.

In some cases it may be desirable to administer the compounds directly to the airways in the form of an aerosol. For administration by intranasal or intrabrochial inhalation, the compounds of this invention may be formulated into an aqueous or partially aqueous solution.

The compounds of this invention may be administered parenterally or intraperitoneally. Solutions or suspensions of these active compounds as a free base or pharmaceutically acceptable salt may be prepared in water suitably mixed with a surfactant such as hydroxyl-propylcellulose. Dispersions may also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of this invention can be administered transdermally through the use of a transdermal patch. For the purposes of this disclosure, thransdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream, such as a semi-permeable membrane covering a reservoir containing the active ingredient with or without a carrier, or a matrix containing the active ingredient. Other occlusive devices are known in the literature.

The compounds of this invention may be administered rectally or vaginally in the form of a conventional suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

In certain embodiments, the present invention is directed to prodrugs. Various forms of prodrugs are known in the art, for example, as discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al. (ed.), "Design and Application of Prodrugs", Textbook of Drug Design and Development, Chapter 5, 113-191 (1991), Bundgaard, et al., Journal of Drug Deliver reviews, 8:1-38 (1992), Bundgaard, J. of Pharmaceutical Sciences, 77:285 et seq. (1988); and Higuchi and Stella (eds.) Prodrugs as Novel Drug Delivery Systems, American Chemical Society (1975).

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

For a more clear understanding, and in order to illustrate the invention more clearly, specific examples thereof are set forth hereinbelow. The following examples are merely illustrative and are not to be understood as limiting the scope and underlying principles of the invention in any way.

The following abbreviations are used: DMSO is dimethylsulfoxide, DMF is N,N-dimethylformamide, NMR is proton nuclear magnetic resonance, and MS is mass spectroscopy with (+) referring to the positive mode which generally gives a M+1 (or M+H) absorption where M=the molecular mass. All compounds are analyzed at least by MS and NMR.

Commercially available reagents and solvents were used directly as received except for N-bromosuccinimide which was recrystallized from water. All procedures employing air- and/or moisture-sensitive reagents were conducted under an inert atmosphere in flame-dried glassware where appropriate. $^1$H NMR spectra were recorded in DMSO-$d_6$ on a Varian Inova spectrometer at 500 MHz, unless otherwise indicated.

EXAMPLE 1

Preparation of N"-{[4-(2-Chlorophenyl)-2-(4-propoxyphenyl)thien-3-yl]acetyl}guanidine Step 1: 2,4-Dibromo-3-methylthiophene (1)

2,3,5-Tribromo-4-methylthiophene (1.00 g, 2.98 mmol) in diethyl ether (20 mL) was cooled to −78° C. n-Butyllithium (1.9 mL, 1.6M, 2.98 mmol) was added dropwise over 5 minutes. After 3 minutes $H_2O$ (5 mL) was added and the solution allowed to warm to room temperature. The ether was dried ($MgSO_4$) and concentrated in vacuo. The resultant residue was distilled (62-64° C., 0.3 torr) to yield 0.62 g (82%) of 2,4-dibromo-3-methylthiophene. $^1$H NMR (500 MHz, DMSO-$d_6$) δ: 2.15 (s, 3H), 7.80 (s, 1H); MS (EI) m/z 254/256/258 (M+.). Anal. Calcd for $C_5H_4Br_2S$: C, 23.46; H, 1.58; N, 0.00. Found: C, 23.92; H, 1.59; N, 0.00

Step 2: 2,4-Dibromo-3-(bromomethyl)thiophene (2)

To a solution of 2,4-dibromo-3-methylthiophene (0.92 g, 3.6 mmol) in carbon tetrachloride was added N-bromosuccinimide (0.64 g, 3.6 mmol) and AlBN (5 mg). The mixture was heated under reflux for 1 h and then for another 4 h in the presence of light. The solution was then cooled to 0° C. and the succinimide was filtered. The residue was washed with carbon tetrachloride. The solvent was removed and the product recrystalized from EtOH to yield 2,4-dibromo-3-(bromomethyl)thiophene (1.08 g, 91%). mp 89-90° C.; $^1$H NMR (500 MHz, DMSO-$d_6$) δ: 4.53 (s, 2H), 7.89 (s, 1H). MS (EI) m/z 332/334/336 (M+.). Anal. Calcd for $C_5H_3Br_3S$: C, 17.93; H, 0.90; N, 0.00. Found: C, 18.02; H, 0.86; N, 0.00.

Step 3: (2,4-Dibromothien-3-yl)acetonitrile (3)

To a solution of 2,4-dibromo-3-(bromomethyl)thiophene (1.00 g, 3.00 mmol) in EtOH (10 mL) was added a solution of potassium cyanide (0.29 g, 4.5 mmol) in $H_2O$ (0.5 mL). The mixture was heated to reflux overnight. The solvent was removed and the residue was partitioned between EtOAc and $H_2O$. The EtOAc was dried ($MgSO_4$) and the solvent removed. The residue was recrystalized from EtOH to yield (2,4-dibromothien-3-yl)acetonitrile (0.72 g, 86%). mp 75.5-77° C.; $^1$H NMR (500 MHz, DMSO-$d_6$) δ: 3.94 (s, 2H), 7.94 (s, 1H). MS (EI) m/z 279/281/283 (M+.). Anal. Calcd for $C_6H_3Br_2NS$: C, 25.65; H, 1.08; N, 4.99. Found: C, 26.04; H, 1.18; N, 4.86.

Step 4: Methyl (2,4-dibromothien-3-yl)acetate (4)

(2,4-Dibromothien-3-yl)acetonitrile (1.1 g, 3.91 mmol) was dissolved in MeOH. Conc. $H_2SO_4$ (0.5 mL) was added and the solution heated to reflux for 14 h. The solvent was removed and the residue was partitioned between EtOAc and $H_2O$. The EtOAc was dried ($MgSO_4$) and the solvent removed. The crude product was purified by Kugelrohr distillation (100° C.) to yield methyl (2,4-dibromothien-3-yl)acetate (1.08 g, 88%). mp 38.5-39° C.; $^1$H NMR (500 MHz, DMSO-$d_6$) δ: 3.65 (s, 3H), 3.69 (s, 2H), 7.84 (s, 1H). MS (EI) m/z 312/314/316 (M+.). Anal. Calcd for $C_7H_6Br_2O_2S$: C, 26.78; H, 1.93; N, 0.00. Found: C, 26.48; H, 1.82; N, 0.00.

Step 5: Methyl [4-bromo-2-(4-propoxyphenyl)thien-3-yl]acetate

Into dioxane (3 mL) was dissolved methyl (2,4-dibromothien-3-yl)acetate (0.355 g, 1.13 mmol) and 4-propoxyphenylboronic acid (0.214 g, 1.19 mmol). $K_2CO_3$ (0.195 g, 1.41 mmol) was dissolved in $H_2O$ (0.4 mL) and added to the dioxane. The solution was degassed by bubbling argon through the mixture for five minutes. {1,1'-Bis(diphenylphosphino)-ferrocene}dichloropalladium(II) complex with dichloromethane (1:1) (0.027 g, 0.033 mmol) was added and the mixture heated under argon to 50° C. for 4 hours (followed by TLC 15:1 Hexane:EtOAc). The solvents were removed and the mixture partitioned between EtOAc and $H_2O$. The EtOAc layer was dried ($MgSO_4$) and absorbed onto silica gel. The product was purified by flash chromatography (25:1 hexane:EtOAc) to yield methyl [4-bromo-2-(4-propoxyphenyl)thien-3-yl]acetate (0.240 g) as a clear oil. $^1$H NMR (500 MHz, DMSO-$d_6$) δ: 0.99 (t, 3H, J=7.32 Hz), 1.75 (m, 2H), 3.65 (s, 5H), 3.98 (t, 2H, J=6.6 Hz), 7.05 (d, 2H, J=8.2 Hz), 7.33 (d, 2H, J=8.2 Hz), 7.72 (s, 1H). MS (ES) m/z 369.0 ([M+H]+). MS (ES) m/z 386.0 ([M+NH4]+).

Step 6: Methyl [4-(2-chlorophenyl)-2-(4-propoxyphenyl)thien-3-yl]acetate

Into dioxane (5 mL) was dissolved [4-bromo-2-(4-propoxyphenyl)thien-3-yl]acetate (0.340 g, 0.92 mmol) and 2-chlorophenylboronic acid (0.287 g, 1.84 mmol). $K_2CO_3$ (0.381 g, 2.76 mmol) was dissolved in $H_2O$ (0.5 mL) and added to the dioxane. The solution was degassed by bubbling argon through the mixture for five minutes. {1,1'-Bis(diphenylphosphino)-ferrocene}dichloropalladium(II) complex with dichloromethane (1:1) (0.027 g, 0.028 mmol) was added and the mixture heated under argon to 70° C. for 3 hours (followed by TLC 15:1 Hexane:EtOAc). The solvents were removed and the mixture partitioned between EtOAc and $H_2O$. The EtOAc layer was dried ($MgSO_4$) and absorbed onto silica gel. The product was purified by flash chromatography (20:1 hexane:EtOAc) to yield methyl [4-(2-chlorophenyl)-2-(4-propoxyphenyl)thien-3-yl]acetate (0.320 g) as a white solid. mp 81-82° C.; $^1$H NMR (500 MHz, DMSO-$d_6$) δ: 1.00 (t, 3H, J=7.48 Hz), 1.75 (m, 2H), 3.46 (s, 2H), 3.98 (t, 2H, J=6.41 Hz), 7.05 (d, 2H, J=8.85 Hz), 7.31 (dd, 1H, J=1.99 and 7.17 Hz), 7.42 (m, 5H), 7.56 (dd, 1H, J=1.22 and 7.78 Hz). MS (ES) m/z 401.1 ([M+H]+). MS (ES) m/z 418.1 ([M+NH4]+). Anal. calcd for $C_{22}H_{21}ClO_3S$: C, 65.91; H, 5.28; N, 0.00. Found: C, 65.54; H, 5.21; N, 0.00.

Step 7: [4-(2-Chlorophenyl)-2-(4-propoxyphenyl)thien-3-yl]acetic acid

Methyl [4-(2-chlorophenyl)-2-(4-propoxyphenyl)thien-3-yl]acetate (0.290 g, 0.725 mmol) was dissolved in EtOH (6 mL). NaOH (2.17 mL, 1N, 2.17 mmol) was added and the solution heated to reflux for 5 h. HCl (2.17 mL, 2N, 4.34 mmol) was added and the solvent removed. The mixture was partioned between EtOAc and $H_2O$. The EtOAc layer was dried ($MgSO_4$) and the solvent removed to yield [4-(2-chlorophenyl)-2-(4-propoxyphenyl)thien-3-yl]acetic acid (0.262 g) as a clear oil. $^1$H NMR (500 MHz, DMSO-$d_6$) δ: 0.95 (t, 3H, J=7.44 Hz), 1.70 (m, 2H), 3.30 (s, 2H), 3.93 (t, 2H, J=6.47 Hz), 6.99 (d, 2H, J=8.78 Hz), 7.28 (dd, 1H, J=1.71 and 7.20 Hz), 7.38 (m, 5H), 7.51 (dd, 1H, J=1.71 and 7.44 Hz), 12.11 (bs, 1H). MS (ES) m/z 387.0 ([M+H]+). MS (ES) m/z 404.1 ([M+NH4]+).

Step 8: N"-{[4-(2-Chlorophenyl)-2-(4-propoxyphenyl)thien-3-yl]acetyl}guanidine

[4-(2-Chlorophenyl)-2-(4-propoxyphenyl)thien-3-yl]acetic acid (0.240 g, 0.62 mmol) was dissolved in DMF (2 mL) and carbonyldiimidizole (0.201 g, 1.24 mmol) was added. The solution was stirred under argon at room temperature for thirty minutes. This solution was slowly added over 1 hour to a solution of quanidine HCl (1.48 g, 15.5 mmol), and diisopropyl ethylamine (2.98 mL, 2.2 g, 17.05 mmol) in DMF (15 mL). After 2 h the solvent was removed, the mixture absorbed onto silica gel and purified by flash chromatography (20:1 EtOAc: 1M $NH_3$ in MeOH) to yield N"-{[4-(2-chlorophenyl)-2-(4-propoxyphenyl)thien-3-yl]acetyl}guanidine (0.184 g) as a white solid. mp 98-99° C.; $^1$H NMR (500 MHz, DMSO-$d_6$) δ: 0.99 (t, 3H, J=7.47 Hz), 1.76 (m, 2H), 3.26 (s, 2H), 3.97 (t, 2H, J=6.56 Hz), 7.00 (d, 2H, J=8.70 Hz), 7.32 (m, 1H), 7.38 (m, 2H) 7.47 (d, 2H, J=8.85 Hz), 7.51 (d, 2H, 7.78 Hz). MS (ESI) m/z 428 ([M+H]+). Anal. calcd for $C_{22}H_{22}ClN_3O_2S\cdot0.20\ H_2O$: C, 61.23; H, 5.23; N, 9.74. Found: C, 60.98; H, 5.30; N, 9.51.

EXAMPLE 2

Preparation of N"-[(2,4-Diphenylthien-3-yl)acetyl]guanidine

This compound was prepared in a fashion similar to Example 1 with the following modifications. Phenyl boronic acid (0.195 g, 1.6 mmol) was used in Step 5 to synthesize methyl (4-bromo-2-phenylthien-3-yl)acetate. This material was reacted as in Example 1 Step 6 with phenyl boronic acid (0.173 g, 1.41 mmol) to synthesize methyl (2,4-diphenylthien-3-yl)acetate which after example 1 Steps 7 and 8 yielded N"-[(2,4-diphenylthien-3-yl)acetyl]guanidine (0.058 g) as a white solid. mp 204-205.5° C.; $^1$H NMR (500 MHz, DMSO-$d_6$) δ: 3.38 (s, 2H), 7.39 (m, 9H), 7.54 (d, 2H, J=8.4 Hz), Anal. Calcd for $C_{19}H_{17}N_3OS\cdot H_2O$: C, 64.57; H, 5.42; N, 11.89. Found: C, 64.98; H, 4.97; N, 11.77.

EXAMPLE 3

Preparation of N"-{[2-(4-Phenoxyphenyl)-4-phenylthien-3-yl]acetyl}guanidine

This compound was prepared in a fashion similar to Example 1 with the following modifications. 4-Phenoxyphenylboronic acid (0.254 g, 1.19 mmol) was used in Step 5 to synthesize methyl [4-bromo-2-(4-phenoxyphenyl)thien-3-yl]acetate. This material was reacted as in Example 1 Step 6 with phenylboronic acid (0.138 g, 1.14 mmol) to synthesize methyl [4-phenyl-2-(4-phenoxyphenyl)thien-3-yl]acetate which after Example 1 Steps 3 and 4 yielded N"-{[2-(4-phenoxyphenyl)-4-phenylthien-3-yl]acetyl}guanidine (0.038 g) as a white solid. mp 116-118° C.; $^1$H NMR (500 MHz, DMSO-$d_6$) δ: 3.38 (s, 2H), 7.04 (d, 2H, J=8.7 Hz), 7.08 (d, 2H, J=8.4 Hz), 7.18 (t, 1H, J=7.4 Hz), 7.42 (m, 8H), 7.54 (d, 2H, J=8.7 Hz). MS (ESI) m/z 428 ([M+H]$^+$). Anal. Calcd for $C_{25}H_{21}N_3O_2S$: C, 70.24; H, 4.95; N, 9.83. Found: C, 69.40; H, 4.83; N, 8.57.

EXAMPLE 4

Preparation of N"-{[4-(2-Chlorophenyl)-2-(4-phenoxyphenyl)thien-3-yl]acetyl}guanidine This compound was prepared in a fashion similar to Example 1 with the following modifications. 4-Phenoxyphenylboronic acid (0.254 g, 1.19 mmol) was used in Step 5 to synthesize methyl [4-bromo-2-(4-phenoxyphenyl)thien-3-yl]acetate. This material was reacted as in Example 1, Step 6 with 2-chlorophenylboronic acid (1.83 g, 11.75 mmol) to synthesize methyl [4-(2-chlorophenyl)-2-(4-phenoxyphenyl)thien-3-yl]acetate (1.55 g) which after Example 1 Steps 7 and 8, yielded N"-{[4-(2-chlorophenyl)-2-(4-phenoxyphenyl)thien-3-yl]acetyl}guanidine (0.33 g) as a white solid. mp 76-78° C.; $^1$H NMR (500 MHz, DMSO-$d_6$) δ: 3.49 (s, 2H), 7.10 (d, 3H, J=8.7 Hz), 7.20 (t, 1H, J=7.33 Hz), 7.33 (m, 1H), 7.44 (m, 5H), 7.51 (m, 3H), 7.57 (dd, 1H, J=7.93 and 1.52 Hz). MS (ESI) m/z 462 ([M+H]$^+$); Anal. Calcd for $C_{25}H_{20}ClN_3O_2S\cdot0.50\ H_2O$: C, 63.76; H, 4.49; N, 8.92. Found: C, 63.69; H, 4.85; N, 9.18.

EXAMPLE 5

Preparation of N"-{[2-(2-Chlorophenyl)-4-(4-propoxyphenyl)thien-3-yl]acetyl}guanidine This compound was prepared in a fashion similar to Example 1 with the following modifications. 2-Chlorophenylboronic acid (1.65 g, 10.5 mmol) was used in Step 5 to synthesize methyl [4-bromo-2-(2-chlorophenyl)thien-3-yl] acetate (2.36 g). This material was reacted as in Example 1, Step 6 with 4-propoxyphenylboronic acid (0.239 g, 1.33 mmol) to synthesize methyl [4-(4-phenoxyphenyl)-2-(2-chlorophenyl)thien-3-yl]acetate (0.290 g) which after Example 1 Steps 7 and 8 yielded N"-{[2-(2-chlorophenyl)-4-(4-propoxyphenyl)thien-3-yl]acetyl}guanidine (0.118 g) as a white solid. mp 111-113° C.; $^1$H NMR (500 MHz, DMSO-$d_6$) δ: 0.99 (t, 3H, J=7.1 Hz), 1.75 (m, 2H), 3.24 (s, 2H), 3.95 (t, 2H, J=6.4 Hz), 6.95 (d, 2H, J=8.8 Hz), 7.37 (m, 3H), 7.45 (m, 2H), 7.52 (d, 1H, J=7.5 Hz), 7.56 (d, 1H, J=8.1 Hz). MS (ES) m/z 428.07 ([M+H]$^+$). Anal. Calcd for $C_{22}H_{22}ClN_3O_2S\cdot0.50\ H_2O$: C, 60.47; H, 5.31; N, 9.62. Found: C, 60.50; H, 5.57; N, 9.46.

EXAMPLE 6

Preparation of N"-({2-(4-Propoxyphenyl)-4-[2-(trifluoromethoxy)phenyl]thien-3-yl}acetyl)guanidine This compound was prepared in a fashion similar to Example 1 with the following modifications. 2-(Trifluoromethoxy)benzeneboronic acid (0.223 g, 1.08 mmol) was used in Step 6 to synthesize methyl {2-(4-propoxyphenyl)-4-[2-(trifluoromethoxy)phenyl]thien-3-yl}acetate. This material was reacted as in Example 1 Steps 7 and 8 to yield N"-({2-(4-propoxyphenyl)-4-[2-(trifluoromethoxy)phenyl]thien-3-yl}acetyl)guanidine (0.076 g) as a white solid. mp 90-92° C.; $^1$H NMR (500 MHz, DMSO-$d_6$) δ: 0.94 (t, 3H, J=7.3 Hz), 1.69 (m, 2H), 3.19 (s, 2H), 3.92 (t, 2H, J=6.4 Hz), 6.94 (d, 2H, J=8.9 Hz), 7.42 (m, 7H). MS (ES) m/z 478.1 ([M+H]$^+$). Anal. Calcd for $C_{23}H_{22}F_3N_3O_3S$: C, 57.85; H, 4.64; N, 8.80. Found: C, 57.01; H, 4.88; N, 9.26.

EXAMPLE 7

Preparation of N-{[4-Phenyl-2-(4-propoxyphenyl)thien-3-yl]acetyl}guanidine

This compound was prepared in a fashion similar to Example 1 with the following modifications. Phenylboronic acid (0.132 g, 1.08 mmol) was used in Step 6 to synthesize methyl [4-phenyl-2-(4-propoxyphenyl)thien-3-yl]acetate. This material was reacted as in Example 1 Steps 7 and 8 to yield N-{[4-phenyl-2-(4-propoxyphenyl)thien-3-yl]acetyl}guanidine (0.041 g) as a white solid. mp 94-95° C.; $^1$H NMR (500 MHz, DMSO-$d_6$) δ: 0.97 (t, 3H, J=7.3 Hz), 1.73 (m, 2H), 3.33 (s, 2H), 3.95 (t, 2H, J=6.5 Hz), 6.96 (d, 2H, J=8.8 Hz), 7.40 (m, 8H). MS (ES) m/z 394.10 ([M+H]$^+$). MS (ES) m/z 787.26 ([2M+H]$^+$). Anal. Calcd for $C_{22}H_{23}N_3O_2S\cdot0.50\ H_2O$: C, 65.65; H, 6.01; N, 10.44. Found: C, 65.79; H, 6.26; N, 10.13.

EXAMPLE 8

Preparation of N"-{[2-Phenyl-4-(4-propoxyphenyl)thien-3-yl]acetyl}guanidine

This compound was prepared in a fashion similar to Example 1 with the following modifications. Phenylboronic acid (0.204 g, 1.68 mmol) was used in Step 5 to synthesize methyl (4-bromo-2-phenylthien-3-yl)acetate (0.271 g). This material was reacted as in Example 1 Step 6 with 4-propoxyphenylboronic acid (0.313 g, 1.74 mmol) to synthesize methyl [2-phenyl-4-(4-propoxyphenyl)thien-3-yl]acetate (0.246 g) which after Example 1 Steps 7 and 8 yielded N''-{[2-phenyl-4-(4-propoxyphenyl)thien-3-yl]acetyl}guanidine (0.088 g) as a white solid. mp 131-132° C.; $^1$H NMR (500 MHz, DMSO-$d_6$) δ: 0.94 (t, 3H, J=7.4 Hz), 1.69 (m, 2H), 3.31 (s, 2H), 3.90 (t, 2H, J=6.5 Hz), 6.89 (d, 2H, J=8.9 Hz), 7.31 (m, 4H), 7.38 (m, 2H), 7.48 (d, 2H, J=8.4 Hz). MS (ES) m/z 394.12 ([M+H]$^+$). MS (ES) m/z 787.30 ([2M+H]$^+$). Anal. Calcd for $C_{22}H_{23}N_3O_2S.0.10\ H_2O$: C, 66.84; H, 5.92; N, 10.63. Found: C, 66.63; H, 5.77; N, 10.36.

EXAMPLE 9

Preparation of N''-{[2-[4-(4-Acetylphenoxy)phenyl]-4-(2-chlorophenyl)thien-3-yl]acetyl}guanidine Step 1: Methyl [4-(2-chlorophenyl)-2-(4-hydroxyphenyl)thien-3-yl]acetate This compound was prepared in a fashion similar to Example 1 with the following modifications: 4(t-Butyldimethylsilyloxy)phenylboronic acid (2.53 g, 10.0 mmol) was used in Step 5 to synthesize methyl [4-bromo-2-(4-{[tert-butyl(dimethyl)silyl]oxy}phenyl)thien-3-yl]acetate (2.71 g). This material was reacted as in Example 1 Step 6 with 2-chlorophenylboronic acid (1.93 g, 12.31 mmol) to synthesize methyl [2-(4-{[tert-butyl(dimethyl)silyl]oxy}phenyl)-4-(2-chlorophenyl)thien-3-yl]acetate (2.12 g). Methyl [2-(4-{[tert-butyl(dimethyl)silyl]oxy}phenyl)-4-(2-chlorophenyl)thien-3-yl]acetate (2.00 g, 4.22 mmol) was dissolved in THF and a solution of tetrabutylammonium fluoride in THF (4.65 mL, 1 M, 4.65 mmol) was added dropwise. The solution was heated to 60° C. and stirred for 3 h. The solvent was removed and the mixture was partitioned between EtOAc and 1N HCl. The EtOAc was washed with $H_2O$, dried (MgSO$_4$), and the solvent removed to yield methyl [4-(2-chlorophenyl)-2-(4-hydroxyphenyl)thien-3-yl]acetate (1.34 g) which was used without further purification.

Step 2

To a solution containing methyl [4-(2-chlorophenyl)-2-(4-hydroxyphenyl)thien-3-yl]acetate (0.50 g, 1.40 mmol) and 4'-fluoroacetophenone (0.195 g, 1.40 mmol) in DMA (5 mL) was added $K_2CO_3$ (0.211 g, 1.53 mmol). The solution was heated to reflux overnight. The solvent was removed and the resulting solid was partitioned between CHCl$_3$ and $H_2O$. The CHCl$_3$ was dried (MgSO$_4$) and the solvent removed to yield methyl [2-[4-(4-acetylphenoxy)phenyl]-4-(2-chlorophenyl)thien-3-yl]acetate (0.41 g) as a white solid.

This material was reacted as in Example 1, Steps 7 and 8 to yield N''-{[2-[4-(4-acetylphenoxy)phenyl]-4-(2-chlorophenyl)thien-3-yl]acetyl}guanidine (0.143 g) as a white solid. mp 117-118° C. $^1$H NMR (500 MHz, DMSO-$d_6$) δ: 2.51 (s, 3H), 3.24 (s, 2H), 7.08 (d, 2H, J=8.8 Hz), 7.14 (d, 2H, J=8.7 Hz), 7.31 (m, 4H), 7.47 (d, 1H, J=8.1 Hz), 7.59 (d, 2H, J=8.7 Hz), 7.96 (d, 2H, J=8.9 Hz). MS (ES) m/z 504.1 ([M+H]$^+$). Anal. Calcd for $C_{27}H_{22}ClN_3O_3S.0.10\ H_2O$: C, 64.11; H, 4.42; N, 8.31. Found: C, 63.88; H, 4.44; N, 8.24.

EXAMPLE 10

Preparation of N''-({4-(2-Chlorophenyl)-2-[4-(4-propionylphenoxy)phenyl]thien-3-yl}acetyl)guanidine Methyl [4-(2-chlorophenyl)-2-(4-hydroxyphenyl)thien-3-yl]acetate was reacted as in Example 9, Step 2 with p-fluoropropiophenone (0.213 g, 1.40 mmol) to yield methyl {4-(2-chlorophenyl)-2-[4-(4-propionylphenoxy)phenyl]thien-3-yl}acetate (0.398 g). This material was reacted as in Example1, Steps 7 and 8 to yield N''-({4-(2-chlorophenyl)-2-[4-(4-propionylphenoxy)phenyl]thien-3-yl}acetyl)guanidine (0.151 g) as a white solid. mp 123-124° C.; $^1$H NMR (500 MHz, DMSO-$d_6$) δ: 1.04 (t, 3H, J=7.2 Hz), 2.98 (q, 2H, J=7.2 Hz), 3.23 (s, 2H), 7.08 (d, 2H, J=8.9 Hz), 7.14 (d, 2H, J=8.7 Hz), 7.31 (m, 4H), 7.47 (d, 1H, J=8.1 Hz), 7.59 (d, 2H, J=8.7 Hz), 7.96 (d, 2H, J=8.9 Hz). MS (ES) m/z 518.10 ([M+H]$^+$).

Anal. Calcd for $C_{28}H_{24}ClN_3O_3S.0.10\ H_2O$: C, 64.70; H, 4.69; N, 8.08. Found: C, 64.66; H, 4.63; N, 7.68.

EXAMPLE 11

Preparation of 2-(4-(2-Chlorophenyl)-2-{4-[2-(1H-pyrazol-4-yl)ethoxy]phenyl}-thien-3-yl)-N-(diaminomethylene)acetamide To a solution of methyl [4-(2-chlorophenyl)-2-(4-hydroxyphenyl)thien-3-yl]acetate (0.485 g, 1.35 mmol), 2-(1H-pyrazol-4-yl)-ethanol (0.166 g, 1.48 mmol), and PPh$_3$ (0.388 g, 1.4 mmol) in THF (3 mL) was added at 0° C. diethyl azo-dicarboxylate (DEAD) (0.265 g, 0.24 mL, 1.52 mmol). The solution was stirred overnight and the solvent removed. The product was purified directly by flash chromatography (20:1 CHCl$_3$:MeOH) to yield methyl (4-(2-chlorophenyl)-2-{4-[2-(1H-pyrazol-4-yl)ethoxy]phenyl}thien-3-yl)acetate (0.565 g). This material was reacted as in Example 1, Steps 7 and 8 to yield 2-(4-(2-chlorophenyl)-2-{4-[2-(1H-pyrazol-4-yl)ethoxy]phenyl}thien-3-yl)-N-(diaminomethylene)acetamide (0.151 g) as a white solid. mp 71-72° C.; $^1$H NMR (500 MHz, DMSO-$d_6$) δ: 2.90 (t, 2H, J=6.7 Hz), 3.50 (s, 2H), 4.15 (t, 2H, J=6.9 Hz), 7.05 (m, 2H), 7.44 (m, 6H), 7.55 (m, 2H), 7.70 (s, 1H). MS (ES) m/z 478.1 ([M–H]$^-$). MS (ES) m/z 538.1 ([M+CH3COO]$^-$). MS (ES) m/z 957.3 ([2M–H]$^-$). Anal. Calcd for $C_{24}H_{22}ClN_5O_2S.H_2O$: C, 57.88; H, 4.86; N, 14.06. Found: C, 55.49; H, 5.37; N, 14.80. A description of 2-(1H-pyrazol-4-yl)-ethanol can be found in Jones and Mann, J. Am. Chem. Soc., 75, 4048-52; 1953.

EXAMPLE 12

Preparation of 2-[4-(2-Chlorophenyl)-2-(4-propoxyphenyl)thien-3-yl]-N-[[(3-hydroxypropyl)amino](imino)methyl]acetamide Step 1

[4-(2-Chlorophenyl)-2-(4-propoxyphenyl)thien-3-yl]acetic acid (0.630 g, 1.62 mmol) was dissolved in CH$_2$CL$_2$ (5 mL) and carbonyldiimidizole (1.31 g, 8.1 mmol) was added. The solution was stirred under argon at room temperature for thirty minutes. 1-H-Pyrazole-1-carboxamidine hydrochloride (2.37 g, 16.2 mmol) and diisopropyl ethylamine (4.23 mL, 3.14 g, 24.3 mmol) were added the solution was stirred overnight. The solvent was removed and the mixture was absorbed onto silica gel and purified by flash chromatography (20:1 CHCl$_3$:MeOH to yield 2-[4-(2-chlorophenyl)-2-(4- propoxyphenyl)thien-3-yl]-N-[imino(1H-pyrazol-1-yl)methyl]acetamide (0.421 g) as a white solid. mp 119-120 ° C.; $^1$H NMR (500 MHz, DMSO-d$_6$) δ: 0.98 (t, 3H, J=7.3 Hz), 1.73 (m, 2H), 3.55 (s, 2H), 3.96 (t, 2H, J=6.4 Hz), 6.53 (m, 1H), 7.02 (d, 2H, J=8.7 Hz), 7.30 (m, 4H), 7.40 (s, 1H), 7.49 (d, 2H, J=8.5 Hz), 7.89 (s, 1H), 8.08 (s, 1H). MS (ES) m/z 479.1 ([M+H]$^+$). MS (ES) m/z 957.2 ([2M+H]$^+$). MS (ES) m/z 979.2 ([2M+NA]$^+$). Anal. Calcd for C$_{25}$H$_{23}$ClN$_4$O$_2$S: C, 62.69; H, 4.84; N, 11.70. Found: C, 62.35; H, 4.86; N, 11.58.

Step 2

To a solution of 2-[4-(2-chlorophenyl)-2-(4-propoxyphenyl)thien-3-yl]-N-[imino(1H-pyrazol-1-yl)methyl]acetamide (0.240 g, 0.50 mmol) in CH$_2$Cl$_2$ (5 mL) was added 3-aminopropanol (0.112 g, 0.12 mL, 1.50 mmol) and diisopropyl ethylamine (0.193 g, 0.26 mL, 1.50 mmol). The solution was stirred overnight at RT. The solvent was removed and the product purified by flash chromatography (15:1 CHCl$_3$: MeOH) to yield 2-[4-(2-chlorophenyl)-2-(4-propoxyphenyl) thien-3-yl]-N-[[(3-hydroxypropyl)amino](imino)methyl]acetamide as a white solid. mp 49-50° C.; MS (ES) m/z 486.09 ([M+H]$^+$). MS (ES) m/z 971.26 ([2M+H]$^+$). Anal. Calcd for C$_{25}$H$_{28}$ClN$_3$O$_3$S.0.10 C$_6$H$_{14}$: C, 62.16; H, 5.99; N, 8.49. Found: C, 62.41; H, 5.70; N, 8.45.

EXAMPLE 13

Preparation of 4-[4-(2-Chlorophenyl)-3-(2-{[[(3-hydroxypropyl)amino](imino)-methyl]amino}-2-oxoethyl)thien-2-yl]-N-(1-ethylpropyl)benzamide Step 1

Pd(PPh$_3$)$_4$ (0.046 g, 0.4 mmol was added to a degassed solution of methyl (2,4-dibromothien-3-yl)acetate (2.51 g, 8 mmol) and 4-carboxybenzeneboronic acid (1.32 g, 8 mmol) in Na$_2$CO$_3$(40 mL, 0.4 M, 16 mmol) and CH$_3$CN (40 mL). The mixture was heated to reflux overnight under argon for 16 h. The solution was filtered hot and the filtrate was concentrated to about half volume. The solution was extracted with CH$_2$Cl$_2$. The aqueous phase was acidified with concentrated HCl and the resulting solid was collected by vacuum filtration and washed with H$_2$O to yield 4-(4-bromo-3-methoxycarbonylmethyl-thiophen-2-yl)-benzoic acid (1.98 g) which was used without further purification.

Step 2

4-(4-Bromo-3-methoxycarbonylmethyl-thiophen-2-yl)-benzoic acid (0.303 g, 0.85 mmol) was dissolved in DMF (2 mL) and carbonyldiimidizole (0.172 g, 1.06 mmol) was added. The solution was stirred at RT for thirty minutes and 3-aminopentane (0.222 g, 2.55 mmol) was added. Stirring was continued for 3 h and the solvent was removed. The mixture was partitioned between EtOAc and H$_2$O. The EtOAc was dried (MgSO$_4$) and the solvent was removed to yield methyl [4-bromo-2-(4-{[(1-ethylpropyl)amino] carbonyl}phenyl)thien-3-yl]acetate (0.248 g) as a white solid. mp 97-98° C.; $^1$H NMR (500 MHz, DMSO-d$_6$) δ: 0.87 (t, 6H, J=7.3 Hz), 1.49 (m, 2H), 1.54 (m, 2H), 3.65 (s, 3H), 3.71 (s, 2H), 3.80 (m, 1H), 7.51 (d, 1H, J=8.5 Hz), 7.85 (s, 1H), 7.95 (d, 2H, J=8.5 Hz), 8.12 (d, 1H, J=8.7 Hz). MS (ES) m/z 424.0 ([M+H]$^+$). MS (ES) m/z 456.0 ([M+CH3OH+ H]$^+$). MS (ES) m/z 847.0 ([2M+H]$^+$). Anal. Calcd for C$_{19}$H$_{22}$BrNO$_3$S: C, 53.78; H, 5.23; N, 3.30. Found: C, 53.65; H, 4.77; N, 3.52.

Step 3

Methyl [4-bromo-2-(4-{[(1-ethylpropyl)amino] carbonyl}phenyl)thien-3-yl]acetate (0.200 g, 0.5 mmol) was dissolved in dioxane (3 mL) and 2-chlorophenylboronic acid (0.156 g, 1.0 mmol). K$_2$CO$_3$ (0.207 g, 1.5 mmol) was dissolved in H$_2$O (0.2 mL) and added to the dioxane. The solution was degassed by bubbling argon through the mixture for five minutes. {1,1'-Bis(diphenylphosphino)-ferrocene}dichloropalladium(II) complex with dichloromethane (1:1) (0.012 g, 0.015 mmol) was added and the mixture heated under argon to 70° C. for 3 hours (followed by TLC 15:1 hexane:EtOAc). The solvents were removed and the mixture partitioned between EtOAc and H$_2$O. The EtOAc layer was dried (MgSO$_4$) and absorbed onto silica gel. The product was purified by flash chromatography (20:1 hexane: EtOAc) to yield methyl [4-(2-chlorophenyl)-2-(4-{[(1-ethylpropyl)amino]carbonyl}phenyl)thien-3-yl]acetate (0.169 g) as a white solid. mp 57-59° C.; $^1$H NMR (500 MHz, DMSO-d$_6$) δ: 0.87 (t, 6H, J=7.3 Hz), 1.50 (m, 2H), 1.55 (m, 2H), 3.35 (s, 3H), 3.53 (s, 2H), 3.75 (m, 1H), 7.31 (d, 1H, J=7.2 Hz), 7.43 (m, 3H), 7.59 (m, 3H), 7.96 (d, 2H, J=8.4 Hz), 8.12 (d, 1H, J=8.7 Hz). MS (ES) m/z456.1 ([M+H]$^+$). MS (ES) m/z488.1 ([M+CH3OH+H]$^+$). MS (ES) m/z 911.2 ([2M+ H]$^+$). Anal. Calcd for C$_{25}$H$_{26}$ClNO$_3$S: C, 65.85; H, 5.75; N, 3.07. Found: C, 65.92; H, 5.96; N, 3.27.

Step 4

Methyl [4-(2-chlorophenyl)-2-(4-{[( 1-ethylpropyl) amino]carbonyl}phenyl)thien-3-yl]acetate (0.145 g, 0.328 mmol) was dissolved in EtOH (2 mL). NaOH (0.65 mL, 1N, 0.65 mmol) was added and the solution heated to reflux for 5 h. HCl (0.35 mL, 2N, 0.70 mmol) was added and the solvent removed. The mixture was partitioned between EtOAc and H$_2$O. The EtOAc layer was dried (MgSO$_4$) and the solvent removed to yield [4-(2-chlorophenyl)-2-(4-{[(1-ethylpropyl) amino]carbonyl}phenyl)thien-3-yl]acetic acid (0.138 g) as a white solid. mp 101-103° C. $^1$H NMR (500 MHz, DMSO-d$_6$) δ: 0.88 (t, 6H, J=7.3 Hz), 1.50 (m, 2H), 1.55 (m, 2H), 3.42 (s, 2H), 3.82 (m, 1H), 7.35 (m, 1H), 7.42 (m, 3H), 7.58 (m, 3H), 7.96 (d, 2H, J=8.4 Hz), 8.11 (d, 1H, J=8.7 Hz). MS (ES) m/z 442.1 ([M+H]$^+$). MS (ES) m/z 883.1 ([2M+H]$^+$). Anal. Calcd for C$_{24}$H$_{24}$ClNO3S: C, 65.22; H, 5.47; N, 3.17. Found: C, 62.33; H, 5.54; N, 3.01.

Step 5

[4-(2-Chlorophenyl)-2-(4-{[(1-ethylpropyl)amino] carbonyl}phenyl)thien-3-yl]acetic acid (0.125 g, 0.282 mmol) was dissolved in CH$_2$Cl$_2$ (2 mL) and carbonyldiimidizole (0.229 g, 1.41 mmol) was added. The solution was stirred under argon at room temperature for 30 min. 1-H-Pyrazole-1-carboxamidine hydrochloride (0.413 g, 2.82 mmol) and diisopropyl ethylamine (0.737 mL, 4.23 mmol) were added to the solution and stirred overnight. The solvent was removed and the mixture was absorbed onto silica gel and purified by flash chromatography (20:1 CHCl$_3$:MeOH) to yield 4-(4-(2-chloro-phenyl)-3-{[(imino-pyrazol-1-yl-methyl)-carbamoyl]-methyl}-thiophen-2-yl)-N-(1-ethyl-propyl)-benzamide (0.087 g) as a white solid.

Step 6

To a solution of 4-(4-(2-chloro-phenyl)-3-{[(imino-pyrazol-1-yl-methyl)-carbamoyl]-methyl}-thiophen-2-yl)-N-(1-ethyl-propyl)-benzamide (0.87 g, 0.16 mmol) in CH$_2$Cl$_2$ (2 mL) was added 3-aminopropanol (0.037 g, 0.040 mL, 0.50 mmol) and diisopropyl ethylamine (0.064 g, 0.087 mL, 0.50 mmol). The solution was stirred overnight at RT. The solvent was removed and the product purified by flash chromatography (15:1 CHCl$_3$:MeOH) to yield 4-[4-(2-chlorophenyl)-3-(2-{[[(3-hydroxypropyl)amino](imino)methyl]amino}-2-oxoethyl)thien-2-yl]-N-(1-ethylpropyl)benzamide (0.047 g) as a white solid. mp 109-110° C. MS (ES) m/z 541.12 ([M+ H]$^+$); Anal. Calcd for C$_{28}$H$_{33}$ClN$_4$O$_3$S.0.60 H$_2$O: C, 60.93; H, 6.25; N, 10.15. Found: C, 60.57; H, 6.07; N, 10.02.

EXAMPLE 14

Preparation of 4-[4-(2-Chlorophenyl)-3-(2-{[[(3-hydroxypropyl)amino](imino)-methyl]amino}-2-oxoethyl)thien-2-yl]-N-(2,2,2-trifluoroethyl)benzamide 4-[4-(2-Chlorophenyl)-3-(2-{[[(3-hydroxypropyl)amino](imino)methyl]amino}-2-oxoethyl)thien-2-yl]-N-(2,2,2-trifluoroethyl)benzamide was prepared in a fashion similar to Example 13 with the following exceptions. 4-(4-Bromo-3-methoxycarbonylmethyl-thiophen-2-yl)-benzoic acid (0.303 g, 0.85 mmol) was reacted with 2,2,2-trifluoroethylamine (0.252 g, 2.55 mol) in Step 2. The synthesis was completed by following Example 13, Steps 3 through 6, to yield 4-[4-(2-chlorophenyl)-3-(2-{[[(3-hydroxypropyl)amino](imino)methyl]amino}-2-oxoethyl)thien-2-yl]-N-(2,2,2-trifluoroethyl)benzamide as a white solid. mp 103-105° C. MS (ES) m/z 553.02 ([M+H]$^+$). Anal. Calcd for $C_{25}H_{24}ClF_3N_4O_3S.0.60$ $H_2O$: C, 53.26; H, 4.51 ; N, 9.94. Found: C, 52.93; H, 4.37; N, 10.01.

EXAMPLE 15

Preparation of 4-[4-(2-Chlorophenyl)-3-(2-{[[(3-hydroxypropyl)amino](imino)-methyl]amino}-2-oxoethyl)thien-2-yl]-N-propylbenzamide 4-[4-(2-Chlorophenyl)-3-(2-{[[(3-hydroxypropyl)amino](imino)methyl]amino}-2-oxoethyl)thien-2-yl]-N-propylbenzamide was prepared in a fashion similar to Example 13 with the following exceptions. 4-(4-Bromo-3-methoxycarbonylmethyl-thiophen-2-yl)-benzoic acid (0.303 g, 0.85 mmol) was reacted with propylamine (0.150 g, 2.55 mmol) in Step 2. The synthesis was completed by following Example 13, Steps 3 through 6 to yield 4-[4-(2-chlorophenyl)-3-(2-{[[(3-hydroxypropyl)amino](imino)methyl]amino}-2-oxoethyl)thien-2-yl]-N-propylbenzamide as a white solid. mp 116-118° C. MS (ES) m/z 513.1 ([M+H]$^+$).

Anal. Calcd for $C_{26}H_{29}ClN_4O_3S.0.10$ $H_2O$: C, 60.65; H, 5.72; N, 10.88. Found: C, 60.33; H, 5.59; N, 10.61.

EXAMPLE 16

Preparation of 4-[4-(2-Chlorophenyl)-3-(2-{[[(3-hydroxypropyl)amino](imino)-methyl]amino}-2-oxoethyl)thien-2-yl]-N-(cyclopropylmethyl)benzamide 4-[4-(2-Chlorophenyl)-3-(2-{[[(3-hydroxypropyl)amino](imino)methyl]amino}-2-oxoethyl)thien-2-yl]-N-(cyclopropylmethyl)benzamide was prepared in a fashion similar to Example 13 with the following exceptions. 4-(4-Bromo-3-methoxycarbonylmethyl-thiophen-2-yl)-benzoic acid (0.303 g, 0.85 mmol) was reacted with (aminomethyl) cyclopropane (0.181 g, 2.55 mmol) in Step 2. The synthesis was completed by following Example 13, Steps 3 through 6, to yield 4-[4-(2-chlorophenyl)-3-(2-{[[(3-hydroxypropyl)amino](imino)methyl]amino-2-oxoethyl)thien-2-yl]-N-(cyclopropylmethyl)benzamide as a white solid. mp 100-101° C.; MS (ES) m/z 525.1 ([M+H]$^+$). Anal. Calcd for $C_{27}H_{29}ClN_4O_3S.0.50$ $H_2O$: C, 60.72; H, 5.66; N, 10.49. Found: C, 60.70; H, 5.86; N, 10.24.

EXAMPLE 17

Preparation of N-Butyl-4-[4-(2-chlorophenyl)-3-(2-{[[(3-hydroxypropyl)amino]-(imino)methyl]amino}-2-oxoethyl)thien-2-yl]benzamide The title compound was prepared in a fashion similar to Example 13 with the following exceptions. 4-(4-Bromo-3-methoxycarbonylmethyl-thiophen-2-yl)-benzoic acid (0.303 g, 0.85 mmol) was reacted with butylamine (0.186 g, 2.55 mmol) in Step 2. The synthesis was completed by following Example 13, Steps 3 through 6, to yield N-butyl-4-[4-(2-chlorophenyl)-3-(2-{[[(3-hydroxypropyl)amino](imino)methyl]amino}-2-oxoethyl)thien-2-yl]benzamide as a white solid. mp 92-95° C. MS (ES) m/z 527.1 ([M+H]$^+$). Anal. Calcd for $C_{27}H_{31}ClN_4O_3S.0.60$ $H_2O$:C, 60.29; H, 6.03; N, 10.42 Found: C, 60.08; H, 5.99; N, 10.32.

EXAMPLE 18

Preparation of 2-[4-(2-Chlorophenyl)-2-(3-methyl-4-propoxyphenyl)thien-3-yl]-N-[[(3-hydroxypropyl)amino](imino)methyl]acetamide Step 1

To a solution of 4.0 gm (0.021 mol) of 4-bromo-2-methylphenol in 300 mL of ethanol was added 1.1 gm (0.028 mol) of NaOH. After dissolution, 2.54 mL (0.028 mol) of 1-bromopropane was added and heated o reflux for 5 h. The solvent was removed at reduced pressure and the residue added to water. The aqueous layer was extracted twice with EtOAc. The combined EtOAc layers were washed twice with water, saturated brine then dried ($Na_2SO_4$) and the solvents removed at reduced pressure. Column chromatography on silica gel (gradient, hexanes to 1% EtOAc-hexanes) yielded 4.7 g (96%) of a colorless oil. This was used without further characterization.

Step 2

To a solution of 4.7 gm (0.02 mol) of 4-bromo-2 methyl-1-propoxybenzene in 60 mL of dry THF at –78° C. was added 10.6 mL of 2.5 M (0.026 mol) n-BuLi over a 5 min period. The solution stirred at –78° C. for 0.25 hr and 6.1 mL (0.026 mol) of triisopropyl borate was added dropwise. The solution stirred at –78° C. for 0.25 h and allowed to warm to room temperature and continue to stir for 18 hr. The solvent was removed at reduced pressure and 10 mL of conc. HCl was added dropwise. The solid was filtered and triturated with hexanes to yield 2.1 gm (53%) of a white solid that was utilized without further purification and characterization.

Step 3

2-[4-(2-Chlorophenyl)-2-(3-methyl-4-propoxyphenyl)thien-3-yl]-N-[[(3-hydroxypropyl)amino](imino)methyl]acetamide was prepared in a fashion similar to Example 1, Steps 5 and 6 and Example 12, Steps 1 and 2 with the following exception. 3-Methyl-4-propoxyphenyl boronic acid (0.49 gm, 2.9 mmol) was used in Example 1, Step 2 to yield a light yellow solid. mp 73-76° C. $^1H$ NMR (500 MHz, $CDCl_3$) δ: 01.03 (t, 3H, J=7.4 Hz), 1.64 (m, 2H), 1.80 (m, 2H), 2.21 (s, 3H), 3.22 (t, 2H, J=6.2 Hz), 3.55 (m, 4H), 3.92 (t, 2H J=6.4 Hz), 6.79 (d, 1H J=8.2 Hz), 7.08 (s, 1H), 7.18-7.41 (m, 6H). MS (ES) m/z 500.11 ([M+H]$^+$). MS (ES) m/z 498.1 [M–H]–. MS (ES) m/z 558.1 [M+$CH_3COO$]–

EXAMPLE 19

Preparation of 2-[4-(2-Chlorophenyl)-2-(2-methyl-4-propoxyphenyl)thien-3-yl]-N-[[(3-hydroxypropyl)amino](imino)methyl]acetamide 2-[4-(2-Chlorophenyl)-2-(2-methyl-4-propoxyphenyl)thien-3-yl]-N-[[(3-hydroxypropyl)amino](imino)methyl]acetamide was prepared in the same fashion as in Example 18, Steps 1 to 3 except that 4-bromo-3-methylphenol was utilized in Step 1. This yielded a light yellow solid. mp 103-105.5° C. $^1$H NMR (500 MHz, CDCl$_3$) δ: 01.07 (t, 3H, J=7.4 Hz), 1.67 (m, 2H), 1.84 (m, 2H), 2.25 (s, 3H), 3.23 (t, 2H, J=6.1 Hz), 3.36 (m, 2H), 3.60 (m, 2H), 3.95 (t, 2H, J=6.7 Hz), 6.76 (m, 2H), 7.19-7.45 (m, 6H). MS (ES) m/z 500.09 ([M+H]$^+$). MS (ES) m/z 498.13 [M−H]−.

EXAMPLE 20

Evaluation of BACE-1 Binding Affinity of Test Compounds

1. Fluorescent Kinetic Assays

Final Assay Conditions: 10 nM human BACE1 (or 10 nM Murine BACE1, 1.5 nM human BACE2), 25 μM substrate (WABC-6, MW 1549.6, from AnaSpec), Buffer: 50 mM Na-Acetate, pH 4.5, 0.05% CHAPS, 25% PBS, room temperature. Na-Acetate was from Aldrich, Cat.# 24,124-5, CHAPS was from Research Organics, Cat. # 1304C 1×, PBS was from Mediatech (Cellgro), Cat# 21-031-CV, peptide substrate AbzSEVNLDAEFRDpa was from AnaSpec, Peptide Name: WABC-6

Determination of stock substrate (AbzSEVNLDAE-FRDpa) concentration: ~25 mM stock solution is made in DMSO using the peptide weight and MW, and diluted to ~25 μM (1:1000) in 1× PBS. Concentration is determined by absorbance at 354 nm using an extinction coefficient ε of 18172 M$^{-1}$cm$^{-1}$, the concentration of stock substrate is corrected, and the substrate stock stored in small aliquots in −80° C. [Substrate Stock]=ABS$^{354\ nm}$*10$^6$/18172 (in mM)

The extinction coefficient ε$^{354\ nm}$ was adapted from TACE peptide substrate, which had the same quencher-fluorophore pair.

Determination of Stock Enzyme Concentration: the stock concentration of each enzyme is determined by absorbance at 280 nm using an ε of 64150 M$^{-1}$cm$^{-1}$ for hBACE1 and MuBACE1, 62870 M$^{-1}$cm$^{-1}$ for hBACE2 in 6 M Guanidinium Hydrochloride (from Research Organics, Cat. # 5134G-2), pH ~6. The extinction coefficient ε$^{280\ nm}$ for each enzyme was calculated based on known amino acid composition and published extinction coefficients for Trp (5.69 M$^{-1}$ cm$^{-1}$) and Tyr (1.28 M$^{-1}$ cm$^{-1}$) residues (*Anal. Biochem.* 182, 319-326).

Dilution and mixing Steps: total reaction volume: 100 μL

2× inhibitor dilutions in buffer A (66.7 mM Na-Acetate, pH 4.5, 0.0667% CHAPS) were prepared, 4× enzyme dilution in buffer A (66.7 mM Na-Acetate, pH 4.5, 0.0667% CHAPS) were prepared, 100 μM substrate dilution in 1× PBS was prepared, and 50 μL 2× Inhibitor, 25 μL 100 μM substrate are added to each well of 96-well plate (from DYNEX Technologies, VWR #: 11311-046), immediately followed by 25 μL 4× enzyme (added to the inhibitor and substrate mix), and the fluorescence readings are initiated.

Fluorescence Readings: Readings at λ$_{ex}$ 320 nm and λ$_{em}$ 420 nm are taken every 40 sec for 30 min at room temperature and the linear slope for substrate cleavage rate (v$_i$) determined.

Calculation of % Inhibition:

% Inhibition =100*(1−v$_i$/v$_0$)

v$_i$: substrate cleavage rate in the presence of inhibitor v$_0$: substrate cleavage rate in the absence of inhibitor IC$_{50}$ Determination:

% Inhibition=((B* IC$_{50}$″)+(100*I$_0$″))/(IC$_{50}$″+I$_0$″)

(Model #39 from LSW Tool Bar in Excel, where B is the % inhibition from the enzyme control, which should be close to 0.) % Inhibition is plotted vs. Inhibitor Concentration (I$_0$) and the data fit to the above equation to obtain IC$_{50}$ value and Hill number (n) for each compound. Testing at least 10 different inhibitor concentrations is preferred. Results are presented below in Table I.

TABLE I

| Example | BACE1 IC$_{50}$ μM |
|---|---|
| 1 | 0.63 |
| 2 | 6.4 |
| 3 | 2.06 |
| 4 | 1.6 |
| 5 | 0.59 |
| 6 | 1.6 |
| 7 | 0.68 |
| 8 | 1.89 |
| 9 | 0.75 |
| 10 | 1.73 |
| 11 | 6.9 |
| 12 | 0.14 |
| 13 | 0.93 |
| 14 | 0.202 |
| 15 | 0.26 |
| 16 | 0.17 |
| 17 | 0.28 |
| 18 | 1.7 |
| 19 | 1.55 |

What is claimed is:

1. A compound of formula I

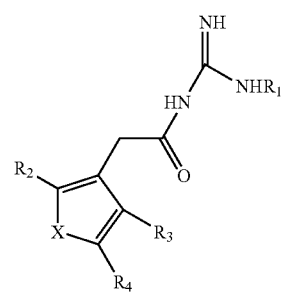

wherein:

X is S;

R$_1$ is hydrogen or an optionally substituted alkyl group;

R$_2$ and R$_3$ are each independently optionally substituted phenyl; and

R$_4$ is hydrogen or an optionally substituted alkyl group; or a tautomer thereof, a stereoisomer thereof or a pharmaceutically-acceptable salt thereof.

2. The compound according to claim 1 wherein R$_1$ is hydrogen.

3. The compound according to claim 1 wherein $R_2$ and $R_3$ are each independently phenyl optionally substituted with one halogen, alkoxy, haloalkoxy, aryloxy or $CONHR_7$, wherein $R_7$ is hydrogen or an alkyl, alkoxy, cycloalkyl, cycloalkenyl, cycloheteroalkyl, aryl, alkyl ester or heteroaryl group.

4. The compound according to claim 1 wherein $R_1$ is hydrogen or an alkyl group optionally substituted with one hydroxy.

5. The compound according to claim 4 wherein $R_2$ and $R_3$ are each independently phenyl optionally substituted with one halogen, alkoxy, haloalkoxy, aryloxy or $CONHR_7$, wherein $R_7$ is hydrogen or an alkyl, alkoxy, cycloalkyl, cycloalkenyl, cycloheteroalkyl, aryl, alkyl ester or heteroaryl group.

6. The compound according to claim 5 wherein $R_4$ is hydrogen.

7. The compound according to claim 1 selected from the group consisting of:
   N"-{[4-(2-chlorophenyl)-2-(4-propoxyphenyl)thien-3-yl]acetyl}guanidine;
   N"-[(2,4-diphenylthien-3-yl)acetyl]guanidine;
   N"-{[2-(4-phenoxyphenyl)-4-phenylthien-3-yl]acetyl}guanidine;
   N"-{[4-(2-chlorophenyl)-2-(4-phenoxyphenyl)thien-3-yl]acetyl}guanidine;
   N"-{[2-(2-chlorophenyl)-4-(4-propoxyphenyl)thien-3-yl]acetyl}guanidine;
   N"-({2-(4-propoxyphenyl)-4-[2-(trifluoromethoxy)phenyl]thien-3-yl}acetyl)guanidine;
   N-{[4-phenyl-2-(4-propoxyphenyl)thien-3-yl]acetyl}guanidine;
   N"-{[2-phenyl-4-(4-propoxyphenyl)thien-3-yl]acetyl}guanidine;
   N"-{[2-[4-(4-acetylphenoxy)phenyl]-4-(2-chlorophenyl)thien-3-yl]acetyl}guanidine;
   N"-({4-(2-chlorophenyl)-2-[4-(4-propionylphenoxy)phenyl]thien-3-yl}acetyl)guanidine;
   2-(4-(2-chlorophenyl)-2-{4-[2-(1H-pyrazol-4-yl)ethoxy]phenyl}thien-3-yl)-N-(diaminomethylene)acetamide;
   2-[4-(2-chlorophenyl)-2-(4-propoxyphenyl)thien-3-yl]-N-[[(3-hydroxypropyl)amino](imino)methyl]acetamide;
   4-[4-(2-chlorophenyl)-3-(2-{[[(3-hydroxypropyl)amino](imino)methyl]amino}-2-oxoethyl)thien-2-yl]-N-(1-ethylpropyl)benzamide;
   4-[4-(2-chlorophenyl)-3-(2-{[[(3-hydroxypropyl)amino](imino)methyl]amino}-2-oxoethyl)thien-2-yl]-N-(2,2,2-trifluoroethyl)benzamide;
   4-[4-(2-chlorophenyl)-3-(2-{[[(3-hydroxypropyl)amino](imino)methyl]amino}-2-oxoethyl)thien-2-yl]-N-propylbenzamide;
   4-[4-(2-chlorophenyl)-3-(2-{[[(3-hydroxypropyl)amino](imino)methyl]amino}-2-oxoethyl)thien-2-yl]-N-(cyclopropylmethyl)benzamide;
   N-butyl-4-[4-(2-chlorophenyl)-3-(2-{[[(3-hydroxypropyl)amino](imino)methyl]amino}-2-oxoethyl)thien-2-yl]benzamide;
   2-[4-(2-chlorophenyl)-2-(3-methyl-4-propoxyphenyl)thien-3-yl]-N-[[(3-hydroxypropyl)amino](imino)methyl]acetamide; and
   2-[4-(2-chlorophenyl)-2-(2-methyl-4-propoxyphenyl)thien-3-yl]-N-[[(3-hydroxypropyl)amino](imino)methyl]acetamide; or
   a tautomer thereof;
   a stereoisomer thereof; or
   a pharmaceutically acceptable salt thereof.

8. A pharmaceutical composition which comprises a pharmaceutically acceptable carrier and an effective amount of a compound of formula I

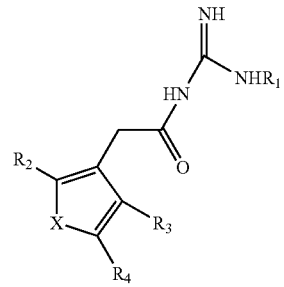

wherein:
   X is S;
   $R_1$ is hydrogen or an optionally substituted alkyl group;
   $R_2$ and $R_3$ are each independently optionally substituted phenyl; and
   $R_4$ is hydrogen or an optionally substituted alkyl group; or
   a tautomer thereof, a stereoisomer thereof or a pharmaceutically-acceptable salt thereof.

9. The composition according to claim 8 wherein $R_1$ is hydrogen or an alkyl group optionally substituted with one hydroxy.

10. The composition according to claim 9 wherein $R_2$ and $R_3$ are each independently phenyl optionally substituted with one halogen, alkoxy, haloalkoxy, aryloxy or $CONHR_7$, wherein $R_7$ is hydrogen or an alkyl, alkoxy, cycloalkyl, cycloalkenyl, cycloheteroalkyl, aryl, alkyl ester or heteroaryl group.

11. The composition according to claim 10 wherein $R_4$ is hydrogen.

12. The composition according to claim 8 having a compound selected from the group consisting of:
   N"-{[4-(2-chlorophenyl)-2-(4-propoxyphenyl)thien-3-yl]acetyl}guanidine;
   N"-[(2,4-diphenylthien-3-yl)acetyl]guanidine;
   N"-{[2-(4-phenoxyphenyl)-4-phenylthien-3-yl]acetyl}guanidine;
   N"-{[4-(2-chlorophenyl)-2-(4-phenoxyphenyl)thien-3-yl]acetyl}guanidine;
   N"-{[2-(2-chlorophenyl)-4-(4-propoxyphenyl)thien-3-yl]acetyl}guanidine;
   N"-({2-(4-propoxyphenyl)-4-[2-(trifluoromethoxy)phenyl]thien-3-yl}acetyl)guanidine;
   N-{[4-phenyl-2-(4-propoxyphenyl)thien-3-yl]acetyl}guanidine;
   N"-{[2-phenyl-4-(4-propoxyphenyl)thien-3-yl]acetyl}guanidine;
   N"-{[2-[4-(4-acetylphenoxy)phenyl]-4-(2-chlorophenyl)thien-3-yl]acetyl}guanidine;
   N"-({4-(2-chlorophenyl)-2-[4-(4-propionylphenoxy)phenyl]thien-3-yl}acetyl)guanidine;
   2-(4-(2-chlorophenyl)-2-{4-[2-(1H-pyrazol-4-yl)ethoxy]phenyl}thien-3-yl)-N-(diaminomethylene)acetamide;
   2-[4-(2-chlorophenyl)-2-(4-propoxyphenyl)thien-3-yl]-N-[[(3-hydroxypropyl)amino](imino)methyl]acetamide;
   4-[4-(2-chlorophenyl)-3-(2-{[[(3-hydroxypropyl)amino](imino)methyl]amino}-2-oxoethyl)thien-2-yl]-N-(1-ethylpropyl)benzamide;

4-[4-(2-chlorophenyl)-3-(2-{[[(3-hydroxypropyl)amino](imino)methyl]amino}-2-oxoethyl)thien-2-yl]-N-(2,2,2-trifluoroethyl)benzamide;

4-[4-(2-chlorophenyl)-3-(2-{[[(3-hydroxypropyl)amino](imino)methyl]amino}-2-oxoethyl)thien-2-yl]-N-propylbenzamide;

4-[4-(2-chlorophenyl)-3-(2-{[[(3-hydroxypropyl)amino](imino)methyl]amino}-2-oxoethyl)thien-2-yl]-N-(cyclopropylmethyl)benzamide;

N-butyl-4-[4-(2-chlorophenyl)-3-(2-{[[(3-hydroxypropyl)amino](imino)methyl]amino}-2-oxoethyl)thien-2-yl]benzamide;

2-[4-(2-chlorophenyl)-2-(3-methyl-4-propoxyphenyl)thien-3-yl]-N-[[(3-hydroxypropyl)amino](imino)methyl]acetamide; and 2-[4-(2-chlorophenyl)-2-(2-methyl-4-propoxyphenyl)thien-3-yl]-N-[[(3-hydroxypropyl)amino](imino)methyl]acetamide; or a tautomer thereof;

a stereoisomer thereof; and a pharmaceutically acceptable salt thereof.

* * * * *